(12) United States Patent
Viola

(10) Patent No.: US 7,371,246 B2
(45) Date of Patent: May 13, 2008

(54) BARREL PINCH FASTENER AND APPLIER

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 591 days.

(21) Appl. No.: 10/491,254

(22) PCT Filed: Oct. 1, 2002

(86) PCT No.: PCT/US02/31299

§ 371 (c)(1),
(2), (4) Date: Mar. 30, 2004

(87) PCT Pub. No.: WO03/030747

PCT Pub. Date: Apr. 17, 2003

(65) Prior Publication Data

US 2004/0199190 A1 Oct. 7, 2004

Related U.S. Application Data

(60) Provisional application No. 60/327,338, filed on Oct. 5, 2001.

(51) Int. Cl.
*A61B 17/08* (2006.01)
*F16K 7/04* (2006.01)

(52) U.S. Cl. .................. 606/158; 606/157; 251/9

(58) Field of Classification Search ............... 606/157, 606/158, 151, 153, 213; 24/535–538, 134 P, 24/132 AA, 115 G; 604/33, 34; 494/29; 251/9

See application file for complete search history.

(56) References Cited

U.S. PATENT DOCUMENTS

| 4,821,996 A | * | 4/1989 | Bellotti et al. ............... 604/34 |
| 4,946,434 A | * | 8/1990 | Plaisted et al. ............... 494/29 |
| 5,282,811 A | | 2/1994 | Booker et al. |
| 5,843,121 A | | 12/1998 | Yoon |
| 5,984,938 A | | 11/1999 | Yoon |
| 6,260,245 B1 | * | 7/2001 | Marsetti ................... 24/115 G |
| 6,589,197 B1 | * | 7/2003 | Doi et al. .................... 604/34 |

* cited by examiner

*Primary Examiner*—Julian W. Woo

(57) ABSTRACT

Surgical fasteners (100) are disclosed for terminating flow of fluid through a body lumen, including an outer barrel (102) having an annular side wall (106) having at least a pair of radial slots (110) formed therein, and an inner barrel (104) rotatably and concentrically coupled within the outer barrel (102). The inner barrel (104) has an annular side wall (118) including a radial slot (122) formed therein corresponding to each radial slot (110) formed in the outer barrel. The surgical fastener (100) has an open position in which the radial slots (110) of the outer barrel (102) are radially aligned with the corresponding radial slots (122) of the inner barrel (104) and a closed position in which the radial slots (110) of the outer barrel (102) are out of radial alignment with the corresponding radial slots (122) of the inner barrel (104) and constrict the body lumen at two locations along the length thereof. An applier (200, 500, 600) is provided for applying the surgical fasteners.

34 Claims, 9 Drawing Sheets

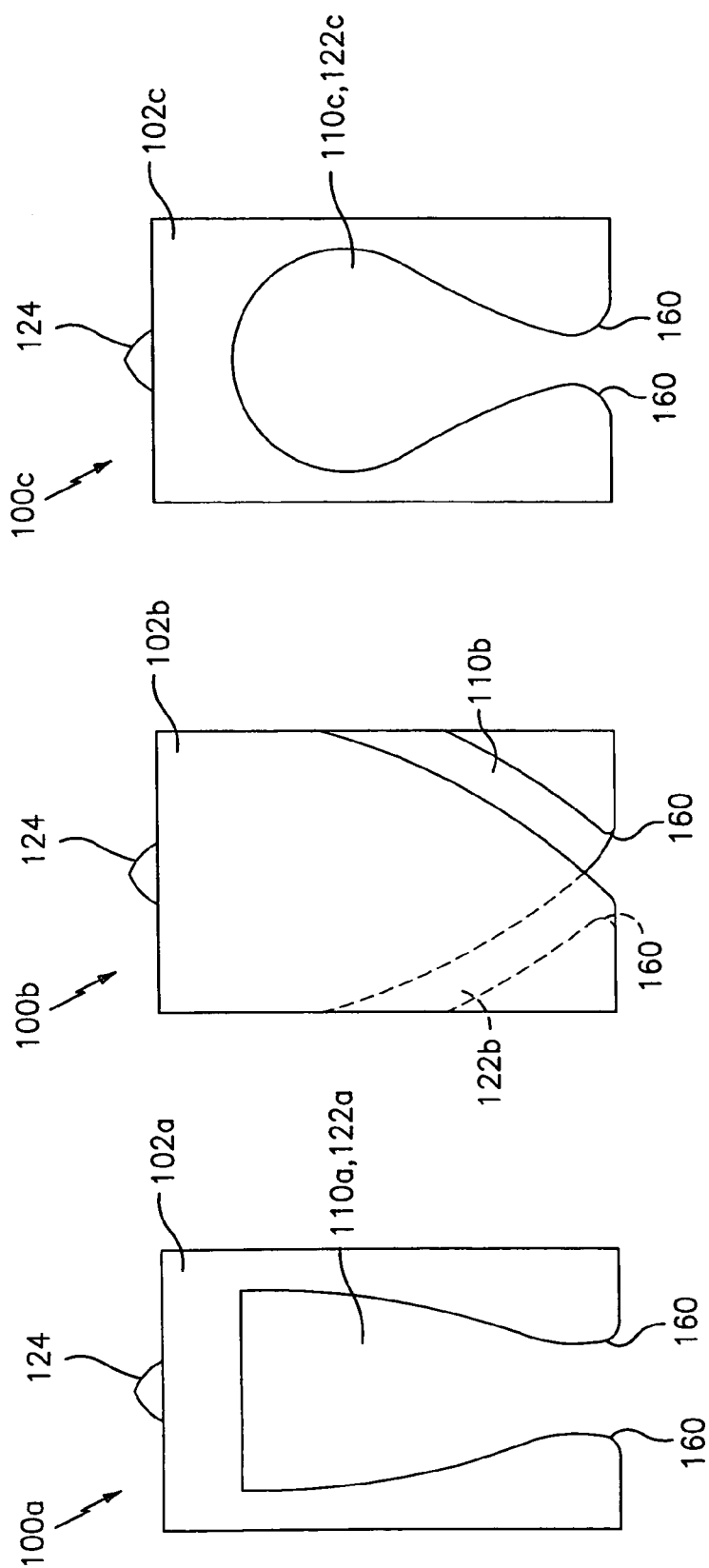

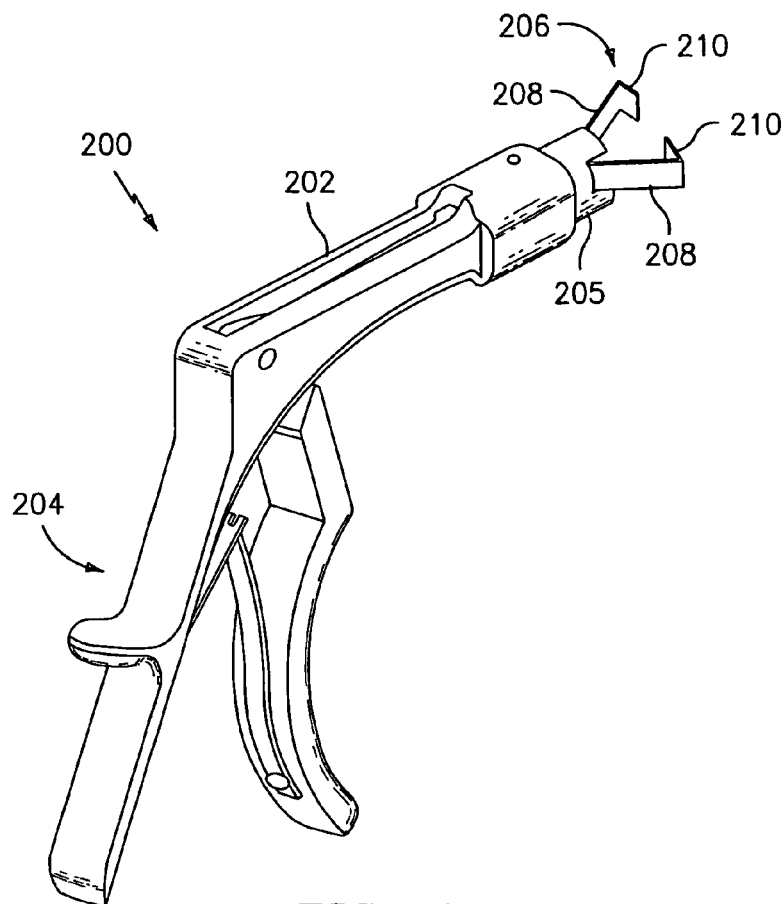
FIG. 4
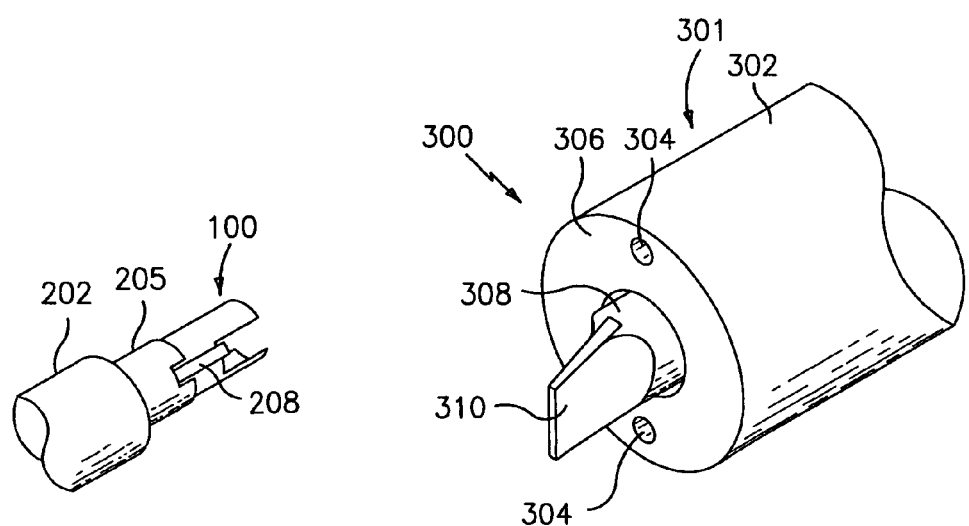
FIG. 4A
FIG. 5

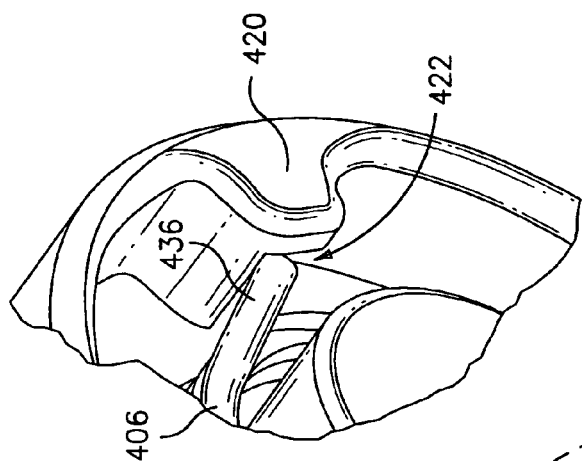
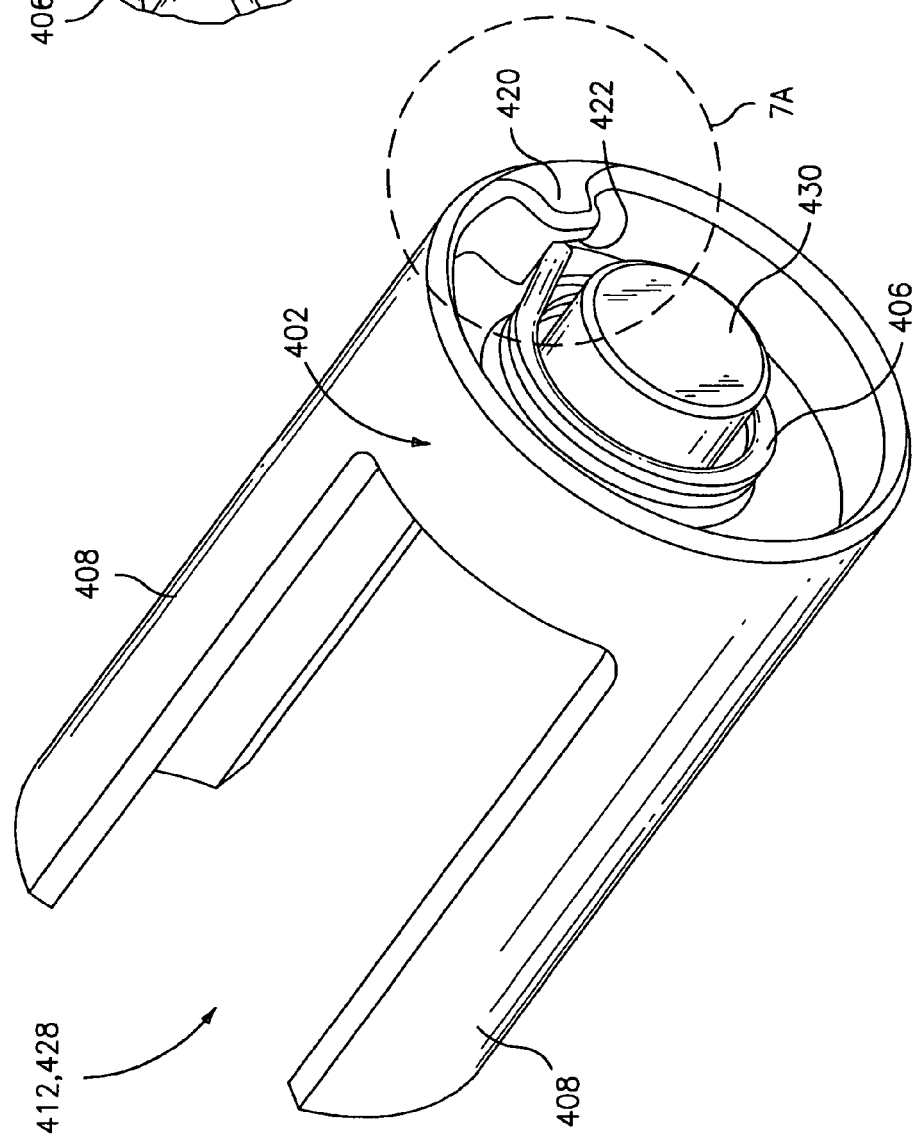

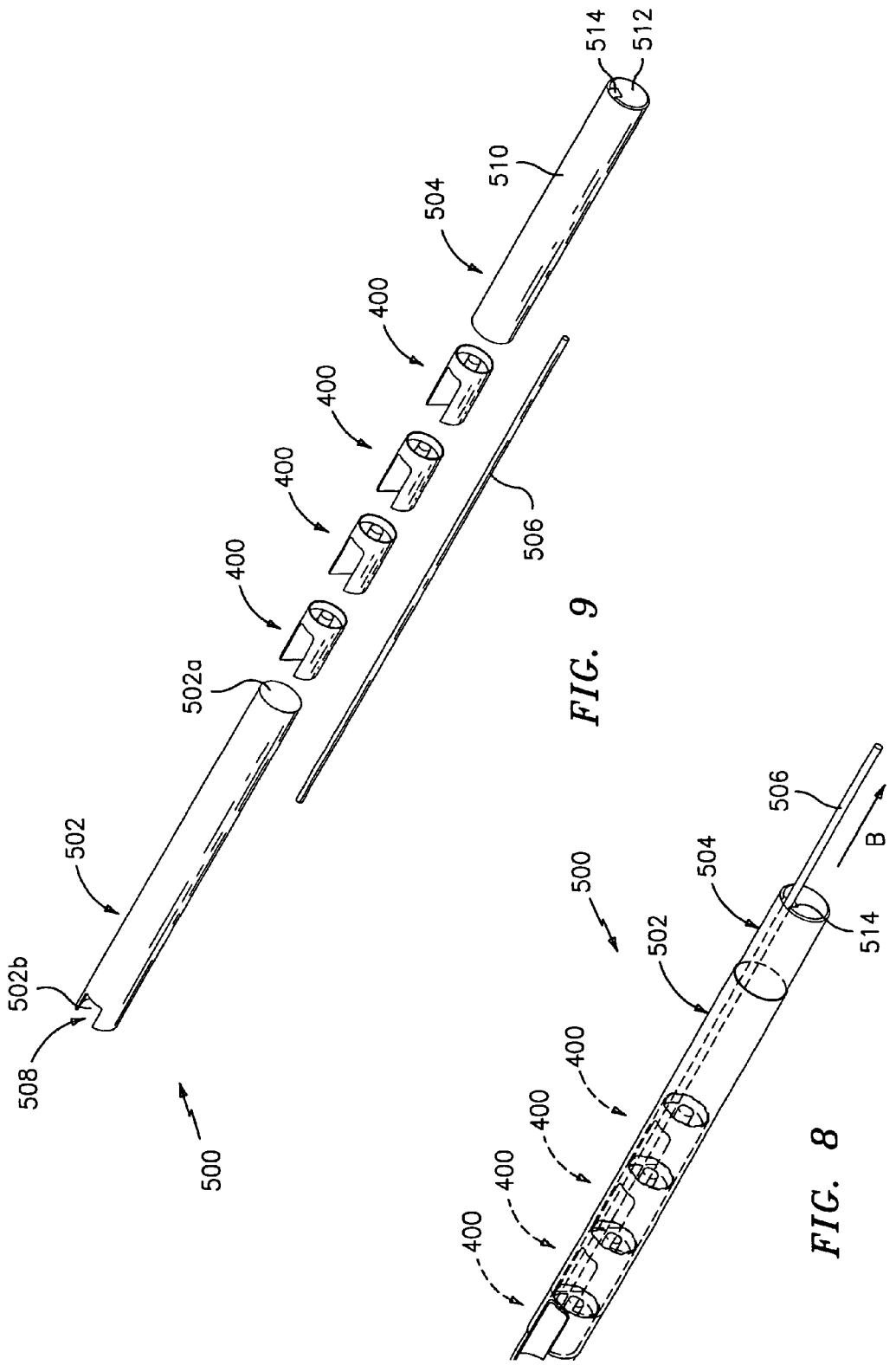

BARREL PINCH FASTENER AND APPLIER

CROSS-REFERENCE TO RELATED APPLICATIONS

The present application claims the benefit of and priority to International Application No. PCT/US02/31299, filed on Oct. 1, 2002, which, in turn, claims the benefit of and priority to U.S. Provisional Patent Application Ser. No. 60/327,338 filed Oct. 5, 2001, the entire contents of each of which are incorporated herein by reference.

BACKGROUND

1. Technical Field

The present disclosure relates to surgical fasteners and, more particularly, to fasteners for simultaneously terminating the flow of fluid through a vessel in two locations along the length of the vessel. In addition, the present disclosure relates to surgical fastener appliers.

2. Background of Related Art

There are many types of surgical fasteners, clips and/or clamps which are used to stop the flow of blood through a vessel or artery. Recently, these fasteners, clips and/or clamps are being used in tubal ligation for female sterilization procedures and in vasectomies for male sterilization. Many of these fasteners, clips and/or clamps are incapable of completely ceasing the flow of fluid through the vessel thereby resulting in the seepage or trickling of fluid through the pinched off area of the vessel. Accordingly, surgeons typically apply two fasteners or clips side-by-side on the vessel to prevent the seepage or trickling of fluid. This seepage is undesirable and can result in medical complications or unwanted or unexpected consequences. For example, in the case of both male and female sterilization, if the male and/or female vessels are not completely sealed against fluid flow, the possibility exists that the female may unexpectedly become impregnated. While the above procedures related to male and female sterilization have been depicted, it is envisioned that similar drawbacks and disadvantages are present with the use of conventional fasteners, clips and/or clamps used in cardiac and vascular procedures in which an artery or other vessel needs to be constricted.

Thus, the need exists for a surgical fastener, which is understood to include a clip or clamp, which effectively terminates fluid flow through a vessel. In addition, the need exists for a surgical fastener which permits a surgeon to operate inside a patient's body via laparoscopic means, under optical guidance, to locate a target vessel and to terminate fluid flow in that target vessel.

SUMMARY

The present disclosure is directed to surgical fasteners for terminating a flow of fluid through a body lumen. The surgical fasteners include an outer barrel having an annular side wall including at least a pair of radial slots formed therein, and an inner barrel rotatably coupled within the outer barrel. Preferably, the inner barrel has an annular side wall including a pair of radial slots formed therein corresponding to a respective one of the radial slots formed in the outer barrel. The surgical fastener has a biased open position in which the radial slots of the outer barrel are radially aligned with the radial slots of the inner barrel and a biased closed position in which the radial slots of the outer barrel and inner barrel are out of radial alignment and constrict the body lumen at two locations along the length thereof Preferably, the fastener includes a spring and the outer barrel and the inner barrel are biased to the closed position. It is envisioned that the outer and inner barrels can be biased in their open positions.

The outer and inner barrels each have an end wall provided at a proximal end thereof and each have an open distal end. Preferably, the slots in each of the outer and inner barrels extend through their respective open distal ends.

In one embodiment, the end wall of the outer barrel includes a central opening formed therethrough and the end wall of the inner barrel includes a snap-fit type engagement member extending outwardly therefrom and through the central opening. Preferably, the engagement member of the inner barrel is snap-fit into and engaged with the central opening formed in the end wall of the outer barrel.

Preferably, the surgical fastener further includes a rotatable biasing element disposed about the snap-fit type engagement member for rotatably biasing the inner and outer barrels to the closed position. The biasing element includes a first leg for engaging a post formed on an outer surface of the end wall of the inner barrel and a second leg for engaging a stop member formed on an inner surface of the end wall of the outer barrel.

The surgical fastener further includes a release rod configured and dimensioned to be removably received within a release hole formed in each of the end walls of the inner and outer barrels. Accordingly, when the release holes are radially aligned with one another and the release rod is received within the release holes, the inner and outer barrels of the fastener are biased in the open position.

In an alternative embodiment the surgical fastener includes an alignment mechanism operatively coupled to the inner and outer barrels to maintain the barrels in alignment and biased in the open position. Preferably, each outer and inner barrel has an end wall provided at a proximal end thereof and has an open distal end in communication with the radial slot of the respective barrels. More preferably, the alignment mechanism includes a hole formed in each end wall wherein the holes are axially alignable when the barrels are in the open position. It is envisioned that the alignment mechanism includes a rod configured and dimensioned to pass through the respective holes when the barrels are in the biased open position, to releasably maintain the barrels in such position.

It is envisioned that the slots have a shape that is either rectangular, tapered, helical or tear-drop. Preferably, the slots have longitudinal edges and the longitudinal edges of the slots of the inner and outer barrels when in the biased closed position terminate fluid flow through the constricted lumen a traumatically.

In an alternate embodiment, the outer barrel includes an annular rim extending proximally from the end wall. The annular rim can include a protrusion extending radially inward therefrom and can define a stop therein. Preferably, the stop is an undercut formed therein.

In the present embodiment, the end wall of the inner barrel includes a central opening formed therethrough and a nub extending from a proximal surface of the end wall. Preferably, the nub is configured and dimensioned to be received within the central opening formed in the end wall of the outer barrel.

The present surgical fastener further includes a biasing element disposed about the nub of the inner barrel for biasing the inner and outer barrels to the closed position. The biasing element can include a first leg in operative engagement with the slot defined by the protrusion of the outer barrel and a second leg in operative engagement with the nub of the inner barrel.

The surgical fastener preferably further includes an alignment mechanism, which preferably includes a release rod configured and dimensioned to be removably received within a release hole formed in each of the end walls of the inner and outer barrels. Accordingly, when the release rod is received within the release holes, the fastener is maintained in the biased open position.

Preferably, in the present embodiment, the central opening of the end wall of the outer barrel includes at least one stop extending radially inward from an inner edge of the central opening and wherein the nub of the inner barrel includes at least one lug extending radially outward therefrom. Preferably, the lug engages the stop in order to prevent free rotation of the inner and outer barrels with respect to one another.

In a preferred embodiment, it is envisioned that the inner barrel is concentric with the outer barrel.

The present disclosure is also related to a surgical fastener applier for applying surgical fasteners to a body lumen. In one embodiment, the surgical fastener applier preferably includes an outer tubular sleeve having an open proximal end, an open distal end and a lumen therethrough, and an inner pusher configured and dimensioned to be reciprocably received within the lumen of the outer tubular sleeve for pushing the fastener toward the distal end of the sleeve and for ejecting the fastener from the sleeve. Preferably, the open distal end of the outer tubular sleeve includes at least one notch, more preferably two notches, extending toward the proximal end of the sleeve. It is envisioned that the outer tubular sleeve is configured and dimensioned to receive at least one surgical fastener in the lumen thereof.

Preferably, the outer diameter of the sleeve is less than about 15 mm, more preferably, less than about 13 mm.

In another embodiment, the surgical fastener applier includes at least one surgical fastener, an outer tubular sleeve including a proximal end and an open distal end and defining a lumen therethrough, the outer tubular sleeve being configured and dimensioned to receive the at least one surgical fastener in the lumen thereof, an inner pusher configured and dimensioned to be reciprocably received within the lumen of the outer tubular sleeve for pushing the fastener toward the distal end of the sleeve, and a mechanism operatively couplable with the fastener for releasably maintaining the fastener in a biased open position. The mechanism can be configured and dimensioned to be reciprocably received within the inner pusher. It is envisioned that the mechanism can be configured and dimensioned such that each surgical fastener has an outer barrel and an inner rotatable barrel. The fastener defines at least a pair of slots extending through the inner and outer barrels and has a biased open position wherein the slots are aligned and a biased closed position wherein the slots are out of alignment.

Preferably, the open distal end of the outer tubular sleeve includes a pair of notches formed therein and extending axially toward the proximal end of the outer tubular sleeve.

It is envisioned that the outer tubular sleeve of the surgical fastener applier includes diametrically opposed notches. The notches preferably extend axially toward the proximal end of the outer tubular sleeve and are radially aligned with the aligned slots of the inner and outer barrels of the surgical fastener when the fastener is in the biased open position at the distal end of the outer tubular sleeve of the applier.

In yet another embodiment, the surgical fastener applier includes a tubular sleeve having a proximal end, an open distal end and a lumen extending through the sleeve and dimensioned to receive a plurality of surgical fasteners therein, the distal end of the sleeve having a pair of opposed notches therein, the notches communicating with the open distal end and extending in a proximal direction into the sleeve, a plurality of surgical fasteners axially aligned in the tubular sleeve, the fasteners having a proximal end and a distal end having a pair of opposed slots in the distal end, an inner pusher configured and dimensioned to be reciprocally received within the lumen of the sleeve, the inner pusher having a distal end that is configured and dimensioned to engage the proximal end of a one of the surgical fasteners and push it distally to the distal end and out of the sleeve, and an alignment mechanism for aligning the surgical fasteners in the tubular sleeve such that when the distal most fastener is at the distal end of the sleeve its slots are aligned with and juxtaposed to the notches of the tubular sleeve.

Preferably, the surgical fastener applier includes holding means for holding the distalmost fastener in the aligned position in the sleeve. The holding means is releasable relative to the distalmost fastener when it is desired to activate or eject the distalmost fastener.

It is contemplated that the applier further includes a loading structure configured and dimensioned to retain a plurality of fasteners therein. The loading structure is configured and dimensioned to be removably received within the tubular sleeve, wherein a plurality of fasteners can be simultaneously loaded into the applier. Preferably, the loading structure includes a pair of diametrically opposed notches formed in a distal end thereof. It is preferred that the notches of the loading structure correspond to the pair of opposed notches formed in the tubular sleeve. The loading structure is preferably configured and dimensioned to slidably receive the inner pusher therein in order to expel the fasteners therefrom.

Other objects and features of the present disclosure will become apparent from consideration of the following description taken in conjunction with the accompanying drawings.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

FIG. 1A is a side elevational view of the barrel pinch fastener of FIG. 1, illustrating an alternative embodiment of the radial slots formed in the inner and outer barrels;

FIG. 1B is a side elevational view of the barrel pinch fastener of FIG. 1, illustrating still another alternative embodiment of the radial slots formed in the inner and outer barrels;

FIG. 1C is a side elevational view of the barrel pinch fastener of FIG. 1, illustrating yet another alternative embodiment of the radial slots formed in the inner and outer barrels;

FIG. 4 is a perspective view of an illustrative barrel pinch fastener applier according to the present disclosure;

FIG. 4A is a perspective view of a distal end of the applier shown in FIG. 4 with a barrel pinch fastener of FIGS. 1-3A shown operatively coupled thereto;

FIG. 5 is an enlarged perspective view of a distal end of an alternative embodiment of a barrel pinch fastener applier according to the present disclosure;

FIG. 7 is an enlarged perspective view of the barrel pinch fastener of FIG. 6, assembled and shown in an open position;

FIG. 7A is an enlarged perspective view of area "7A" of FIG. 7, depicting the engagement of torsion spring within an undercut formed in a receiving protrusion of the outer barrel;

FIG. 8 is a top perspective view of an extended body portion of a barrel pinch fastener applier according to an alternate embodiment of the disclosure;

FIG. 9 is an exploded view of the components of the extended body portion of the barrel pinch fastener applier shown in FIG. 8.

DETAILED DESCRIPTION OF PREFERRED EMBODIMENTS

Figure 1:
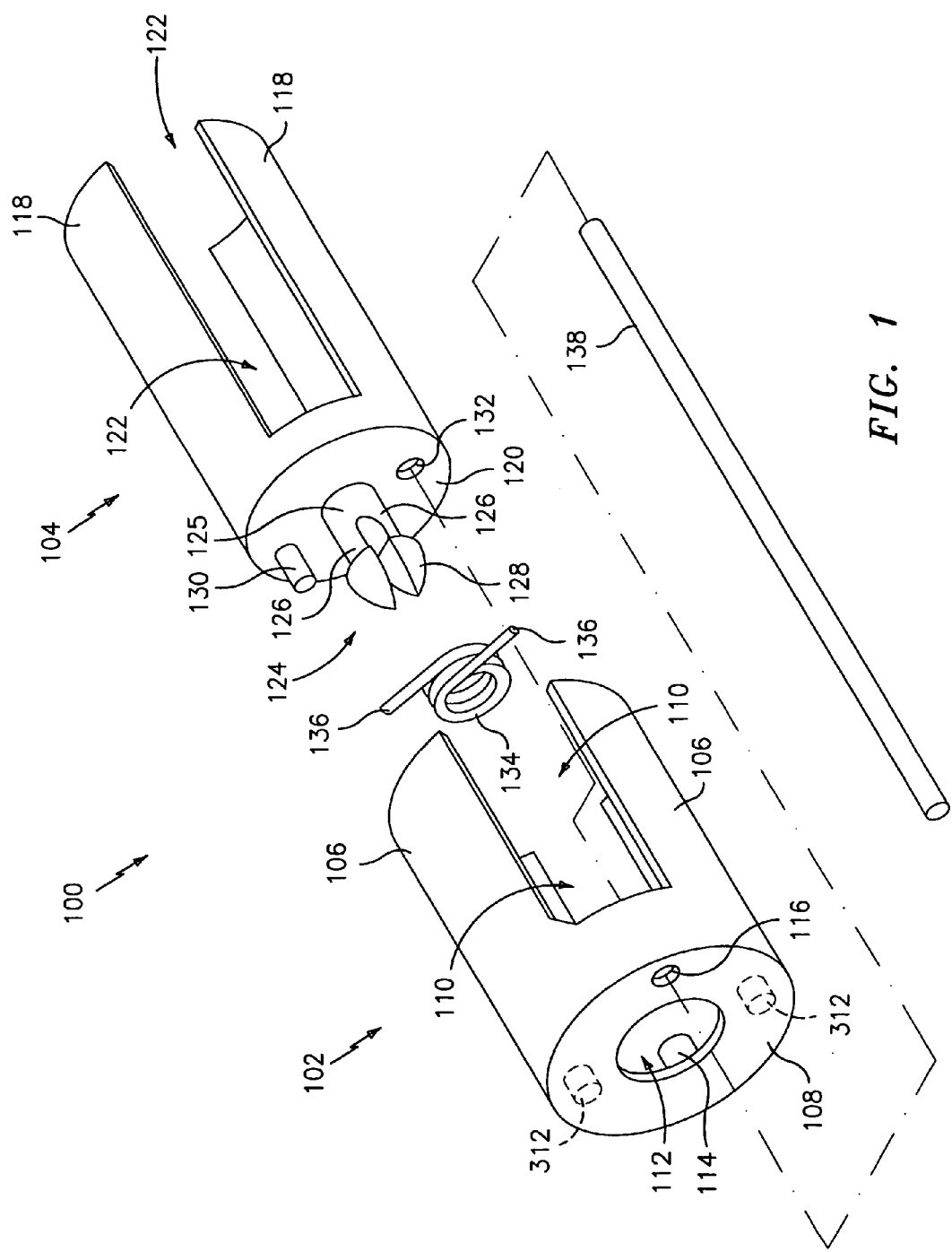
FIG. 1 is an exploded perspective view of a barrel pinch fastener according to the present disclosure.

Preferred embodiments of the presently disclosed barrel pinch fasteners and appliers are described in detail herein with reference to the drawing figures wherein like reference numerals identify similar or identical elements. In the drawings and in the description which follows, the term "proximal", as is traditional will refer to the end of the electrosurgical instrument which is closest to the operator, while the term "distal" will refer to the end of the instrument which is furthest from the operator.

Figure 2:
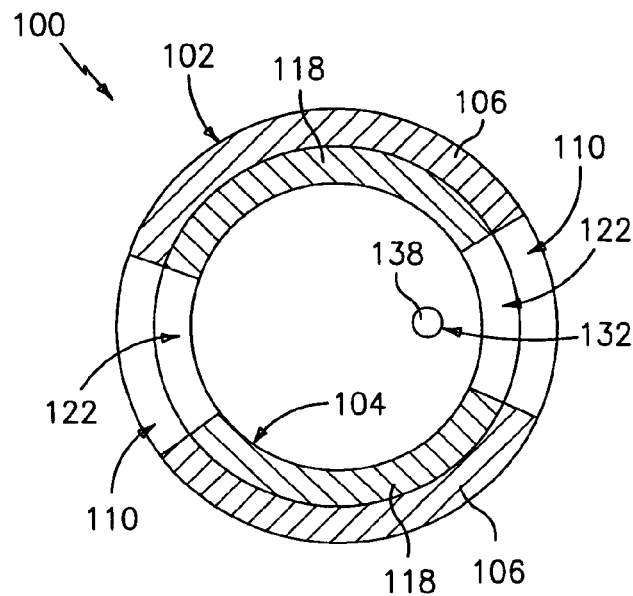
FIG. 2 is a vertical sectional view as would be seen of the barrel pinch fastener of FIG. 1, assembled and shown in an open position.
Figure 3:
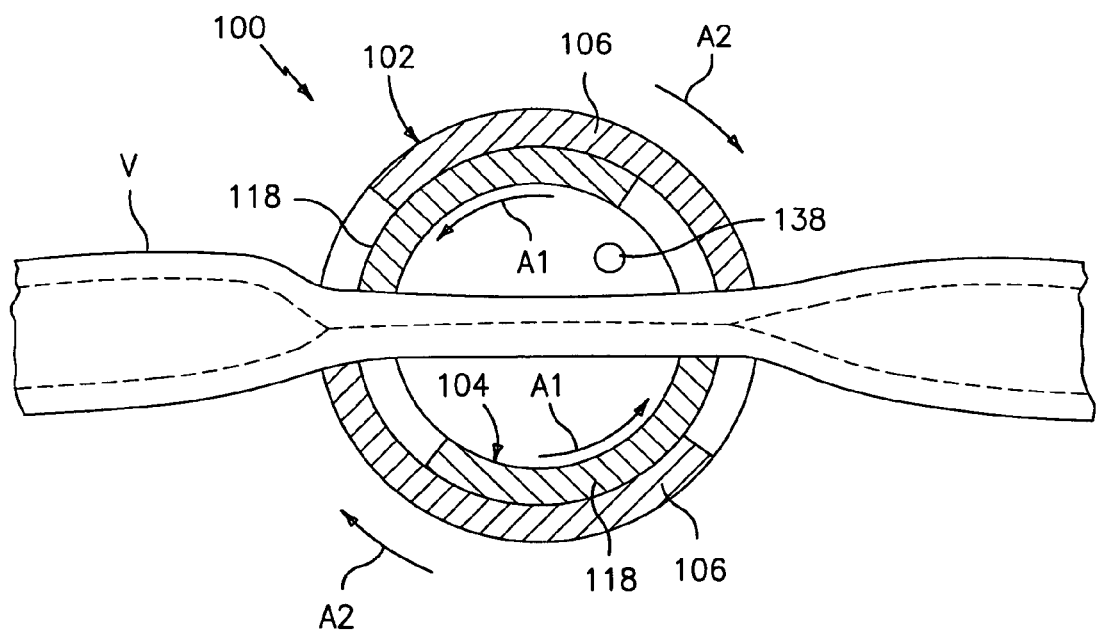
FIG. 3 is a vertical sectional view as would be seen of the barrel pinch fastener of FIG. 1, assembled and shown in a closed position about a vessel passing therethrough.
Figure 3A:
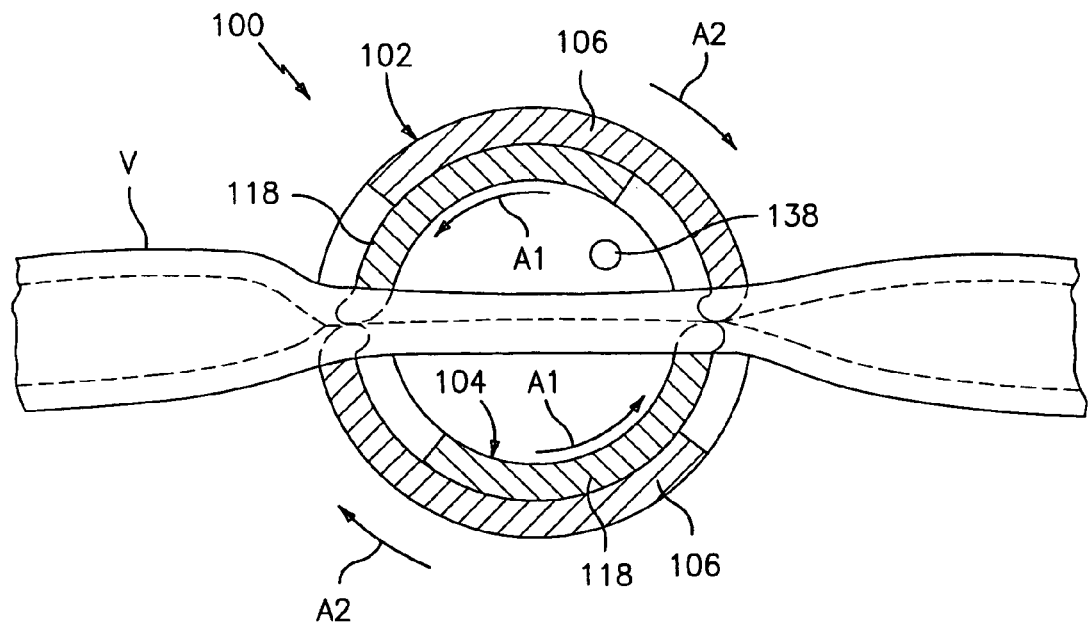
FIG. 3A is a vertical sectional view as would be seen of the barrel pinch fastener of FIG. 2A, assembled and shown in a closed position about a vessel passing therethrough.

Referring now in detail to FIGS. 1-3A, in which like reference numerals identify similar or identical elements, a barrel pinch fastener in accordance with the present disclosure is generally designated as 100. As shown in FIG. 1, fastener 100 includes an outer barrel 102 and an inner barrel 104 adapted to be rotatably coupled concentrically within outer barrel 102. FIGS. 2-3A show inner barrel 104 rotatably coupled within outer barrel 102. Preferably, inner barrel 104 is concentric relative to outer barrel 102.

Outer barrel 102 includes an annular side wall 106 capped at a first end by an end wall 108 and open at a second end. Annular side wall 106 is provided with a pair of opposed cut outs or radial through slots 110 preferably beginning from a distance spaced from end wall 108 and extending through the open end of annular side wall 106. In this embodiment, a longitudinal axis of each radial through slot 110 is oriented in a direction parallel to a longitudinal axis of outer barrel 102. Slots 110 preferably are diametrically or radially aligned. While a pair of radial slots 110 is shown, it is envisioned that any number of through slots of any suitable configuration can be provided.

End wall 108 is provided at its center with a through hole 112 which is aligned with the longitudinal axis of outer barrel 102. In addition, end wall 108 is provided with a spring post 114 extending from an inner surface thereof and into the interior of outer barrel 102. Post 114 has a spring retaining undercut (not shown) for maintaining an arm 136 of a spring 134 in operative engagement with post 114. End wall 108 also includes a release hole 116 formed therein. Release hole 116 is located radially between through hole 112 and side wall 106.

Inner barrel 104 includes an annular side wall 118 capped at a first end by an end wall 120 and open at a second end. Side wall 118 is provided with a pair of opposed cut outs or radial through slots 122 beginning from a distance below end wall 120 and extending through the open end of annular side wall 118. A longitudinal axis of each radial through slot 122 is oriented in a direction parallel to a longitudinal axis of inner barrel 104. Slots 112 preferably are diametrically or radially aligned. While a pair of radial slots 122 is shown, it is envisioned that any number of through slots of any suitable configuration can be provided.

End wall 120 is provided with a split pin 124 integrally formed and extending from the center of end wall 120. Split pin 124 is aligned with a central longitudinal axis of inner barrel 104. Split pin 124 includes a trunk portion 125, a plurality, preferably a pair of legs 126 extending from trunk portion 125 and an enlarged head portion 128 formed on the end of each leg 126. Trunk portion 125 has a diameter smaller than a diameter of hole 112 formed in end wall 108 of outer barrel 102 while the head portions 128 have a combined diameter, when uncompressed, which is larger than the diameter of hole 112.

Inner barrel 104 has an outer diameter slightly smaller than the inner diameter of outer barrel 102. Thus, in order to couple inner barrel 104 to outer barrel 102, the capped end of inner barrel 104 is inserted into the open end of outer barrel 104, and pressed forward so that split pin 124 enters the arcuate opening of tension spring 134, and so that split pin 124 contacts an inner rim of the center through hole 112. By pressing inner barrel 104 further into outer barrel 102, the heads 128 of each leg 126 act like cams and cause legs 126 to deflect until split pin 124 is fully inserted into hole 112, at which time each leg 126 returns to its un-deflected orientation thereby locking inner barrel 104 into outer barrel 102 (i.e., a snap-fit type coupling). In this manner, inner barrel 104 and outer barrel 102 are free to rotate about one another.

In addition, end wall 120 of inner barrel 104 is provided with a spring post 130 extending from an outer surface thereof, and preferably also has an undercut or over-cut for purposes previously explained. End wall 120 also includes a release hole 132 formed therein. Hole 132 is formed radially between split pin 124 and annular side wall 118.

Torsion spring 134 includes a pair of outwardly extending arms 136. Preferably, arms 136 extend tangentially, although they could extend radially. Preferably, torsion spring 134 is disposed on split pin 124 of inner housing barrel 104. Other types of springs as a resilient or restrictive means that provides a rotational bias are envisioned, such as, an elastomeric disc, and a compression or extension spring. In this manner, when inner barrel 104 is inserted into outer barrel 102, a first arm 136 of torsion spring 134 engages spring post 114 of outer barrel 102 while a second arm 136 of torsion spring 134 engages spring post 130 of inner barrel 104. In this manner, as inner barrel 104 is rotated about split pin 124, spring posts 114 and 130 cause torsion spring 134, barrels 102 and 104 and barrel pinch fastener 100 to become biased toward the closed position.

Barrel pinch fastener 100 has a first biased open position (FIG. 2, 2A) in which radial slots 110 of outer barrel 102 are aligned with radial slots 122 of inner barrel 104, a second less-biased vessel occluding position in which radial slots 110 of outer barrel 102 and radial slots 122 of inner barrel 104 are out of alignment with one another thereby partially closing barrel pinch fastener 100 and partially occluding a vessel positioned therebetween, and a final unbiased closed position (FIGS. 3, 3A) in which radial slots 110 of outer barrel 102 are "closed" by annular walls 118 of inner barrel 104 and wherein radial slots 122 of inner barrel 104 are "closed" by annular walls 106 of outer barrel 102. The barrel pinch fastener 100 preferably is maintained in the first biased open position by aligning release hole 116, 514 formed in outer barrel 102 with release hole 132 formed in inner barrel 104, and passing a release rod 138, 506 (FIGS. 1, 7, 8 and 9) therethrough. In order to activate barrel pinch fastener 100, release rod 138, 506 is removed from release holes 116, 132, 514 thereby permitting biased outer barrel and inner barrel 102 and 104, and 402, 404 to rotate about one another, thus allowing radial slots 110 and 122, and 412, 428 to close.

In use in a surgical procedure, referring, for example, to the first embodiment of the barrel pinch fastener of the invention, barrel pinch fastener 100 is maintained in the first open biased position, as by release rod 138, wherein radial slots 110 are aligned with radial slots 122. A vessel "V" (FIGS. 3 and 3A) is then inserted into the aligned radial slots 110 and 122. With vessel "V" in place in slots 110, 122 of barrel pinch fastener 100, release rod 138 is removed from holes 116, 132 and inner and outer barrels 102, 104 are thereby released from the restraint of their bias and permitted to rotate in opposite biased directions about one another as depicted by arrows "A1" and "A2" in FIGS. 3 and 3A. As seen in FIG. 3, in so doing, a length of the vessel corresponding to a width, i.e., the extent of the opening, of radial slots 110 and 122 is reduced, i.e., basically closed, around vessel "V", thereby simultaneously constricting or pinching vessel "V" at two diametrically opposed locations (left and right), thereby there preventing or terminating all fluid flow through vessel "V".

In addition, barrel pinch fastener 100 is shown as having an inner barrel 104 and an outer barrel 102, each of which is respectively provided with radial slots 122, 110 that are defined by smooth edges. Preferably, whether made of metal or plastic, the edges of slots 110, 122 are atraumatic (i.e., rounded or smooth), see FIG. 7, and are not burred. Nevertheless, it is envisioned that the longitudinal edges of radial slots 110, 122 can have matching or offset undulations or indentations or can be provided with a series of teeth or gaps and teeth formed along a portion or the entire length thereof. In this manner, barrel pinch fastener 100 is better able to grip the targeted vessel and resist the potential for the vessel to slip out of the free open end of the barrel pinch fastener.

Preferably, radial slots 110 and 122 have parallel side edges and are parallel to one another, as shown. However, it is envisioned that either one or preferably both radial slots 110 and 122 can have a modified shape, for example, those shown in FIGS. 1A-1C. In FIG. 1A, an alternate barrel pinch fastener 100*a* is shown including tapered slots 110*a,* 122*a* formed in outer barrel 102*a* and in the inner barrel (not shown). In FIG. 1B, another alternate barrel pinch fastener 100*b* is shown including helical slots 110*b,* 122*b* formed in outer barrel 102*b* and in the inner barrel (not shown). In FIG. 1C, still another alternate barrel pinch fastener 100*c* is shown including tear-drop slots 110*c,* 122*c* formed in outer barrel 102*c* and in the inner barrel (not shown). Preferably, shaped slots 110*a*-110*c* and 122*a*-122*c* (hereinafter, for simplicity, "shaped slots 110, 122") of barrel pinch fasteners 100*a*-100*c* include rounded or atraumatic distal terminal ends 160.

Preferably, shaped slots 110, 122 have a larger width toward or near each capped end of the outer and inner barrels, and a smaller width near the free or open end of the outer and inner barrels. In this manner, as the outer and inner barrels rotate about one another and close on the target vessel, the distal, narrower edge surfaces of each shaped slot 110, 122 act to draw and/or retain the vessel rearwardly toward the capped end of barrel pinch fastener 100*a*-100*c* and the tips of shaped slots 110, 122 abut or overlap one another. As such, vessel "V" is prevented from slipping out of the open free end of barrel pinch fasteners 100*a*-100*c*. The helical, tapered or tear-drop shaped slots 100, 122 do not unduly restrict the mouth of the combined opening, yet provide closure of the inner and outer barrels at their distal ends.

Figure 2A:
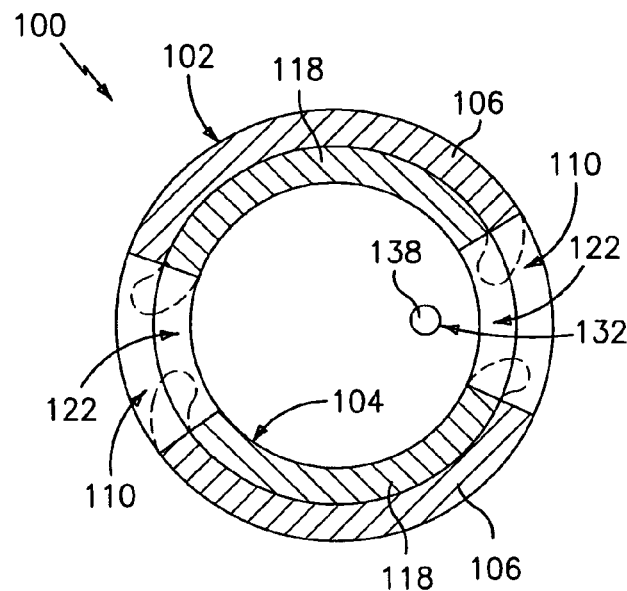
FIG. 2A is a vertical sectional view as would be seen of a barrel pinch fastener, assembled and shown in an open position, and being provided with cooperative pinching edges along respective slots thereof.

Further, as shown by the dashed lines in FIGS. 2A and 3A, the respective cooperative pinching edges of slots 110 and 122 can be directed toward each other so that the faces of the pinching edges partly or fully overlap and abut each other when the barrel fastener is in a still biased closed position without a vessel therebetween. With a vessel within the slots, the faces of the cooperative pinching edges will be partly or fully juxtaposed and will pinch the vessel between the faces.

Barrel pinch fastener 100 can be constructed from any biologically inert material such as plastic, metal (i.e., stainless steel, titanium) or the like. Barrel pinch fastener 100 can also be constructed of a bioabsorbable material. It is envisioned that the preferred method of fabricating the components of the barrel fastener is by injection molding.

Figure 6A:
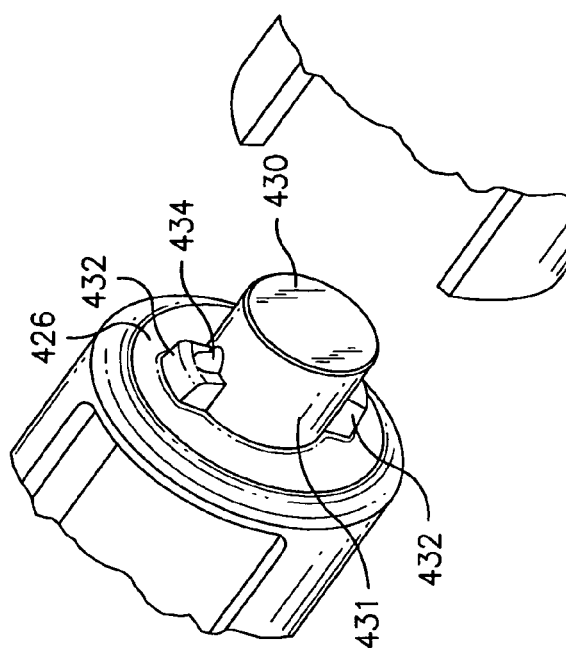
FIG. 6A is an enlarged perspective view of area "6A" of FIG. 6, depicting the nub provided on the end wall of the inner barrel.
Figure 6:
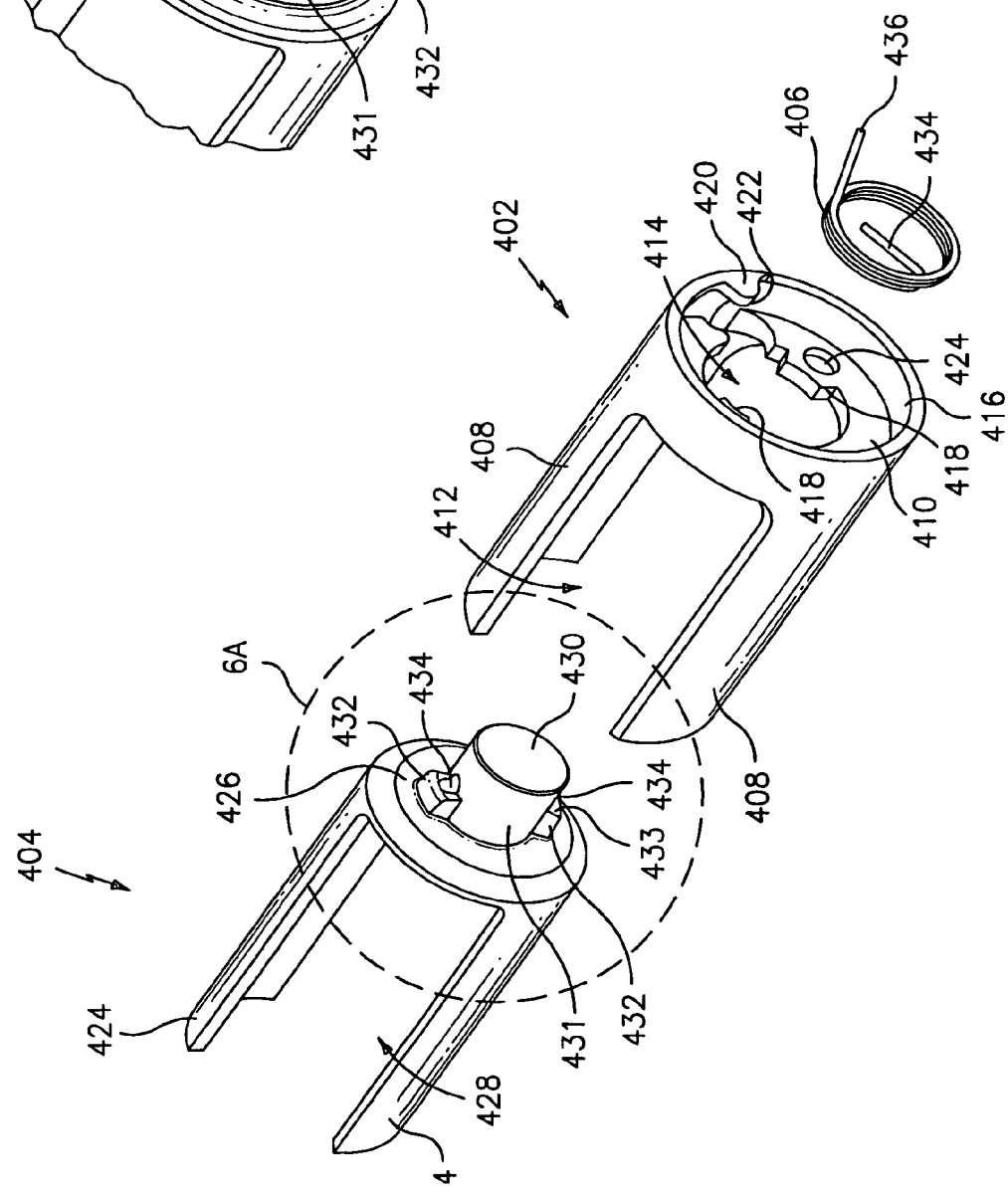
FIG. 6 is an exploded perspective view of another embodiment of a barrel pinch fastener according to the present disclosure.

Turning now to FIGS. 6 and 7, a barrel pinch fastener according to another, preferred embodiment of the present disclosure is shown generally as 400. In FIG. 6, barrel pinch fastener 400 includes an outer barrel 402 and an inner barrel 404 axially aligned with one another and adapted to be rotatably coupled concentrically within outer barrel 402. In FIG. 7, the outer barrel 402 and inner barrel 404 are in operative engagement with one another via torsional spring 406.

Outer barrel 402 includes an annular side wall 408 capped at a first end by an end wall 410 and open at a second end thereof. Annular side wall 408 is provided with a pair of opposed cut outs or radial through slots 412 beginning from a distance spaced from end wall 410 and extending through the open end of annular side wall 408. As in the above described embodiment, in this present embodiment, a longitudinal axis of each radial through slot 412 is oriented in a direction parallel to a longitudinal axis of outer barrel 402. Slots 412 are preferably diametrically or radially aligned. While a pair of slots 412 has been shown, it is envisioned that any number of through slots of any suitable configuration can be provided.

Outer barrel 402 includes a center through hole 414 formed at a center of end wall 410, which hole 414 is aligned with the longitudinal axis of outer barrel 402, and an annular rim 416 extending axially from side wall 408. Hole 414 is partly defined by a pair of radially inwardly extending diametrically opposed stops 418 formed along the edge thereof. As seen in FIGS. 6-7A, and in detail in FIG. 7A, rim 416 includes a radially inwardly extending protrusion 420 having a spring retaining slot or undercut 422 formed therein. End wall 410 further includes a release hole 424 formed therein. Release hole 424 is located radially between hole 414 and rim 416.

Inner barrel 404 includes an annular side wall 424 capped at a first end by an end wall 426 and which is open at a second end. Side wall 424 is provided with a pair of opposed cut-outs or radial through slots 428 beginning adjacent to or, as shown, extending from end wall 426 and through the open end of annular side wall 424. A longitudinal axis of each radial through slot 428 is oriented in a direction parallel to a longitudinal axis of inner barrel 404. Slots 428 preferably are diametrically or radially aligned with one another. While a pair of slots 428 is shown, it is envisioned that any number of through slots of any suitable configuration can be provided.

As seen in FIGS. 6 and 6A, end wall 426 is provided with a nub 430 extending axially outward from the surface of end wall 426. Nub 430 has a cylindrical side wall 431 and at least one, preferably a pair of opposed lugs 432. Preferably, the pair of opposed lugs 432 are diametrically opposed and extend radially from side wall 431 and axially from end wall 426. Nub 430 preferably is hollow and/or includes at least one through hole 434 extending completely radially through side wall 431 in at least one location thereof. Hole 434 preferably also extends through the outer face wall 433 of at least one, preferably both, of the lugs 432, so that hole 434 preferably extends through side wall 431 and at least one, preferably both, lugs 432. Preferably hole 434 passes through the pair of opposed lugs 432. Inner barrel 404 further includes a release hole (not shown) formed in end wall 426 between nub 430 and annular side wall 424.

Inner barrel 404 has an outer diameter slightly smaller than the inner diameter of outer barrel 402. Thus, in order to couple inner barrel 404 to outer barrel 402, the closed end of inner barrel 404 is inserted into the open end of outer barrel 404, and pressed forward so that nub 430 enters hole 414. It is envisioned that nub 430 can be either hollow or solid and while nub 430 has been shown as being cylindrical, it is envisioned that nub 430 can have any suitable shape.

Torsion spring 406 includes a pair of arms, a first arm 434 extending radially inward and a second arm 436 extending tangentially outward from torsional spring 406. With inner barrel 404 inserted in outer barrel 402 (FIG. 7), first arm 434 of spring 406 is inserted through hole 434 formed in side wall 431 of nub 430 and second arm 436 of spring 406 is operatively coupled to, i.e., seated in, cut-out 422, here shown formed in provision 420 extending radially inwardly from rim 416 of outer barrel 402. FIG. 7 shows barrel pinch fastener 400 in its fully biased open position.

In operation, inner barrel 404 is rotated within outer barrel 402 until release hole 424 of outer barrel 402 is aligned with the release hole (not shown) of the inner barrel 404, thereby biasing torsional spring 406. As in the prior embodiment, a release rod 138 is passed through release holes 424 to bias barrel pinch fastener 400 in the open position. By aligning release holes 424, slots 412 of outer housing 402 are also aligned with slots 428 of inner housing 404. Inner barrel 404 is prevented from freely rotating within barrel 402 by release rod 138 and by the engagement of lugs 432 formed on nub 430 with stops 418 formed along the rim of hole 414. It is envisioned that the engagement of lugs 432 with stops 418 can be at any position after the vessel occluding position and before the spring disengages from the spring retaining slot 422.

The spring of barrel pinch fastener 100, which biases inner and outer barrels 104, 102 in opposite rotational directions, will pinch release rod 138 and with application of sufficient spring force, will hold or maintain barrel pinch fastener 100 in sleeve 502.

Turning now to FIGS. 8 and 9, an extended distal portion, e.g., an endoscopic portion, 501 of a barrel pinch fastener applier 500 is shown. Extended distal portion 501 includes an outer tubular sleeve 502 preferably having open proximal and distal ends 502a, 502b, respectively, an inner pusher 504 which is coaxial and reciprocable within sleeve 502 and a release rod 506. Tubular herein means enclosed or substantially enclosed. Preferably, sleeve 502 is fully enclosed, although it can be substantially enclosed, that is, less than fully enclosed. For example, for a cylindrical sleeve, a sleeve portion thereof can be enclosed a suitable extent within the range of from about 340° to about 360°. Outer tubular sleeve 502 defines a lumen therethrough. While shown as cylindrical, it is envisioned that the pusher 504 can have any desired shape.

Sleeve 502 is open ended at each end and has an inner diameter slightly larger than the outer diameter of outer barrels 102, 402 and preferably has a length sufficient to pass through and be utilizable through an incision, trocar, e.g. a 15 mm or 13 mm trocar or surgical port, e.g., for laparoscopic or endoscopic uses, and sufficient to accommodate a plurality of barrel pinch fasteners 100, 400 therewithin. Sleeve 502 has a proximal end 502a and a distal end 502b, and preferably includes a pair of diametrically opposed notches 508 (one shown) formed at the distal end. Notches 508 have a width which preferably is at least substantially equal to the width of aligned slots 412 and 428 of outer and inner barrels 402 and 404 respectively. It is envisioned that slots 412, 428 need not be the same width as each other or as notches 508 in sleeve 502.

Pusher 504 includes an annular side wall 510 and distal and proximal end walls 512 (proximal end shown). Pusher 504 and end walls 512 are provided with a through hole or channel opening 514 formed therethrough for receiving a release rod 138, 506 therein. Pusher 504 can have one or more loops extending radially inward from the internal diameter of the pusher and defining an opening 514, or a pusher 504 can have a channel attached to or integral with pusher wall 510 for channeling release rod 138, 506. Alternatively, pusher 504 can have an axial groove extending radially into the outer surface of the barrel pinch fastener that corresponds with a protrusion or key extending axially, above and radially inwardly from the internal diameter of sleeve 502. Pusher 504 has an outer surface that is slightly smaller than the inner diameter of the sleeve 502. Opening 514 formed in the end wall 512 is radially spaced from side wall 510 such that opening 514 preferably axially aligns with the release holes formed in the outer and inner barrel end walls. While a solid pusher with a through bore extending the entire length of the pusher has been disclosed, it is envisioned that a hollow pusher having capped ends and/or suitable means for holding a release rod can also be used. It is contemplated that the holding means can include, for example, a hole and rod structure (i.e., the hole being formed in the fastener and the rod extending therethrough), a slot and key structure and the like.

In order to load the extended distal portion 501 of applier 500, release rod 138, 506 (hereinafter, for simplicity, "release rod 506") is inserted completely through opening 514 of pusher 504 and extended out of the distal end thereof, a first barrel pinch fastener 100, 400 (hereinafter, for simplicity, "barrel pinch fastener 400") is coupled to release rod 506 by aligning the release holes of the outer and inner barrels and sliding release rod 506 into the aligned release holes of the barrel pinch fastener. Any number of barrel pinch fasteners 400 can be aligned and coupled to release rod 506 in the same manner. With all of the barrel pinch fasteners 400 coupled to release rod 506, release rod 506 and coupled barrel pinch fasteners 400 are inserted into sleeve 502 and slid forward to the distal end thereof until slots 412 and 428 of first barrel pinch fastener 400 are aligned with notches 508. While circular release holes have been disclosed, it is envisioned that a shaped slot can be provided for receiving a correspondingly shaped release rod.

In order to apply a barrel pinch fastener 400 using extended distal portion 501 of surgical applier 500, a target vessel is inserted into notches 508 of sleeve 502 and slots 412 or 438 of barrel pinch fastener 400. Then, or simultaneously, either release rod 506 is withdrawn in direction "B" (See FIG. 8) from first barrel fastener 400, or pusher 504 is pushed forward thereby distally urging first barrel pinch fastener off of release rod 506, or a combination of the two steps can be employed. With first barrel pinch fastener 400 removed from applier 500, pusher 504 automatically or otherwise urges the distal most or any of the remaining fasteners forward toward the distal end of applier 500 so that the next, i.e., distal most, barrel pinch fastener 400 is seated in a firing position at the distal end thereof and is ready to be applied to a target vessel.

A major advantage of the barrel pinch fastener is that it applies a double seal on a vessel, while a major advantage of the applier discussed above for applying the barrel pinch fastener is that it is much less complicated than conventional appliers and is less expensive to produce. By employing a single tube and a rod, much less squeeze force is required to drive or push a pusher axially to push a barrel pinch fastener off of a release rod and out of the applier, and/or to withdraw a rod from openings in the end walls of the respective barrels of the barrel pinch fastener.

Another advantage of the barrel pinch fasteners of the present invention is that the endoscopic portion of the fastener appliers for the fasteners can have a smaller diameter in order to fit 13 mm trocars. Whereas conventional clip appliers often require jaws which extend radially outward of the outer tubular portion of the endoscopic portion to surround and squeeze clip of fastener onto a vessel to be ligated, the barrel pinch fasteners of the present invention in more preferred embodiments with appliers, do not require such jaws and wider diameter trocars.

Yet another advantage of the barrel pinch fastener and applier of the invention is that the distal end of the barrel pinch fastener and/or of the extended portion of the applier can advantageously be used for blunt dissection of tissue prior to, during or after applying a barrel pinch fastener, without damage or deformation of portions of the applier.

The barrel pinch fasteners can be made of any suitable shape and configuration. The outer surface of the barrel pinch fastener need not be cylindrical, but can be polygonal, rectilinear, oblong, oval, etc.

The barrel pinch fasteners are maintained or held in position against rotation of the barrels so that their slots are axially and radially aligned with notches 508 in sleeve 502 by any suitable means including, e.g., an inward detent or bulge on the inside surface of the sleeve and a cooperating slot or depression on the outside of the barrel fastener. It is also envisioned that another set of release holes and another rod can pass therethrough, on an opposite quadrant of the barrel pinch fastener than the other rod, to prevent its rotation relative to the outer sleeve. Also, it is envisioned that cooperative frictional surfaces on the outer sleeve and inner sleeve can be provided. It is further envisioned that sleeve 502 include suitable means, e.g., a radially inwardly protruding lip or one or more detents, to prevent the distal most fastener from inadvertently leaving the end of the sleeve.

Turning now to FIGS. 4, 4A and 5, while barrel pinch fastener 100 has been described as operating in conjunction with a release rod, it is also envisioned that a barrel pinch fastener according to the present disclosure can be operated or applied with the aid of a surgical fastener applier. A surgical fastener applier according to an alternative embodiment of the present disclosure is generally depicted as 200. Applier 200 includes a body portion 202, a pair of handles 204 spring biased in an open position, a jaw mount 205 and a pair of jaws 206 which are biased in a closed position when handles 204 are in an open spaced apart position. In operation, when handles 204 are squeezed together to a closed position, jaws 206 separate to an open position.

Each of jaws 206 includes a leg portion 208 and a foot portion 210 extending orthogonally to leg portion 208. Each foot portion 210 is oriented toward one another. Jaws 206 have a thickness, i.e. height, slightly smaller than a width of a radial slot of a the barrel pinch fasteners disclosed herein.

Thus, as used in combination with a barrel pinch fastener according to the present disclosure, the inner and outer barrels of a barrel pinch fastener are rotated to align the radial slots formed in each. Handles 204 of applier 202 are squeezed together thereby opening the pair of jaws 206. A barrel pinch fastener is inserted between the pair of jaws 206 with the open end of the barrel pinch fastener oriented away from applier 200 and each radial slot aligned with a respective jaw 206. Handles 204 are then released so that foot portions 210 of the pair of jaws 206 enter the radial slots thereby maintaining the barrel pinch fastener in an open position.

In operation, the surgeon advances applier 200 with the barrel pinch fastener thereon or therein, toward a target vessel such that the target vessel will enter into the aligned slots of the inner and outer barrels. If the surgeon is satisfied with the positioning of the barrel pinch fastener with respect to the target vessel, the surgeon squeezes handles 204 of applier 200, thereby causing the pair of jaws 206 to release the barrel pinch fastener causing the torsion spring to rotate the inner barrel and outer barrel in opposite directions. This rotation causes the slots to narrow until the target vessel is totally pinched-off, in two separate locations, side-by-side, thus terminating all fluid flow in the vessel.

As seen in FIG. 5, an alternative barrel fastener applier according to the present disclosure is shown as 300. Barrel pinch fastener applier 300 has a distal end 301 that includes an outer sleeve 302 having a pair of opposed recesses 304 formed on an end face 306 thereof and a central shaft 308 extending through a center of end face 306 and having a tapered flattened distal end portion 310. Outer sleeve 302 and central shaft 308 shown in FIG. 5 are intended to be shown as and are independently rotatable with respect to one another and wherein central shaft 308 is retractable within outer sleeve 302.

Barrel pinch fastener applier 300 can operate in conjunction with a modified version of barrel pinch fastener 100 disclosed above. The modified barrel pinch fastener (not shown in FIG. 5) can include a pair of opposed lugs 312 (dashed lines in FIG. 1) extending outwardly from end wall 108 of outer barrel 102 (See FIG. 1). Each lug 312 is configured and adapted to be inserted into recesses 304 of outer sleeve 302. Moreover, the flattened distal end portion 310 of central shaft 308 is configured and adapted to engage the slot defined by the pair of legs 126 of split pin 124 (FIG. 1).

Thus, as used in combination with a barrel pinch fastener according to the present disclosure, a so-modified barrel pinch fastener 100 is coupled to the end of barrel pinch fastener applier 300 such that split pin 124 engages the flattened forward portion 310 of central shaft 308. With inner barrel 104 being held in place, outer barrel 102 is rotated until the pair of opposed lugs 312 are aligned with recesses 304 formed on outer sleeve 302 and are then inserted into recesses 304 thereby maintaining outer barrel 102 in a biased position with respect to inner barrel 104 and with radial slots 110 and 122 aligned with one another. The surgeon then advances the applier/fastener combination toward a target vessel such that the target vessel will enter into the aligned slots of the inner and outer barrels. If the surgeon is satisfied with the positioning of barrel fastener with respect to the target vessel, the surgeon pulls back on central shaft 308, effectively disengaging the flattened distal end portion 310 from split pin 124. With the flattened distal end portion 310 removed, inner barrel 104 is free to rotate due to the action of the torsion spring 134 thereby pinching the vessel between radial slots 110 and 122.

The procedure is fully reversible to thereby remove the barrel pinch fastener from the vessel "V". To remove the barrel pinch fastener once recesses 304 of fastener applier 300 are fitted over lugs 312 of outer barrel 102, flattened forward portion 310 is aligned with and inserted into the slot between the head or legs 126 of split pin 124 and central shaft 308 is rotated to thereby realign radial slots 110 and 122 with one another and thereby release the vessel.

Figure 10:
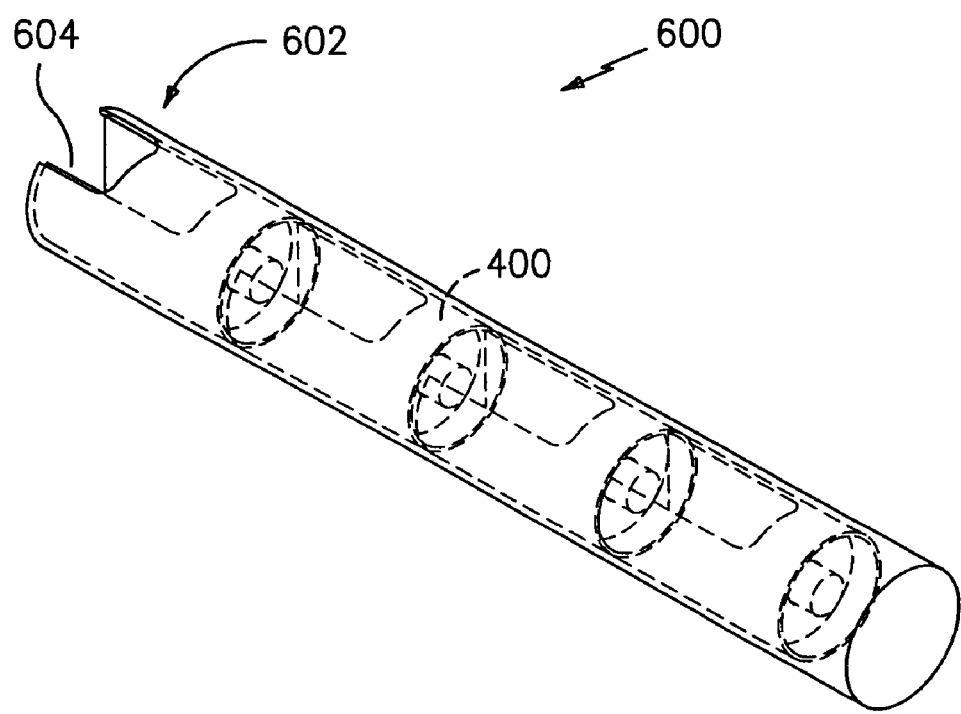
FIG. 10 is an enlarged perspective view of a loading structure, in accordance with the present disclosure, containing a plurality of fasteners therein.

As seen in FIG. 10, it is envisioned that multiple, preferably aligned, barrel pinch fasteners 400 may be provided in or on a pre-loaded cartridge, magazine or other loading structure 600 to facilitate rapid loading, pre-loading or re-loading of an applier, such as, for example, applier 500, with a plurality of fasteners 400. Loading structure 600 can correspond to the shape of the sleeve and can sit in a pocket therein. Preferably, a distal end 602 of loading structure 600 will have diametrically or otherwise disposed notches 604 therein that will correspond to the notches in the sleeve, or, if the sleeve does not have notches, those of loading structure 600 can extend beyond the distal end of the sleeve and serve to permit application of fasteners 400 directly from loading structure 600 onto the vessel to be occluded.

Once loading structure 600 has been emptied of all of its fasteners 400, a new loading structure 600 can be loaded into applier 500. As such, applier 500 can be reused by simply removing the used and/or spent loading structure 600 and replacing it with a new loading structure 600 having a full compliment of fasteners 400 therein.

It is also envisioned, that in using a barrel fastener of the invention, if a higher fluid pressure is anticipated or a more resilient vessel is to be pinched-off, a torsion spring having a larger spring coefficient can be used in the barrel fastener. It is understood that although the biasing structure preferably provides an increasing force or bias, alternative biasing structures that provide a constant force can be employed. In addition, while a torsion spring has been disclosed and described, it is envisioned that other biasing means or rotational means may be used to cause the inner barrel to rotate with respect to the outer barrel. For example, an elastomeric disc can be attached to and used to bias the barrels relative to one another.

It will be understood that appliers of the invention can include holding means for holding the distalmost fastener in the aligned position in the sleave, the holding means being releasable relative to the distalmost fastener when it is desired to activate or eject the distalmost fastener. Holding means here means those means, structures and/or mechanisms disclosed herein and their equivalents by which the applier holds the inner and outer barrels of one or more fasteners in alignment, including, fastener with fastener, slots with slots, and preferably also slots with notches.

It will be further understood that various modifications may be made to the embodiments disclosed herein. Therefore, the above description should not be construed as limiting, but merely as an exemplification of preferred embodiments. Those skilled in the art will envision other modifications within the scope and spirit of the claims appended hereto.

What is claimed is:

1. A surgical fastener for terminating a flow of fluid through a body lumen, comprising:
    an outer barrel having an annular side wall including at least a pair of radial slots formed therein and defining an open end;
    an inner barrel rotatably coupled within the outer barrel, the inner barrel having an annular side wall including a pair of radial slots formed therein and defining an open end, wherein the coupled inner and outer barrels are open ended in a common direction, each radial slot of the pair formed in the side wall of the inner barrel corresponding to a respective one of the radial slots formed in the outer barrel;
    wherein the surgical fastener has a biased open position in which the radial slots of the outer barrel are radially aligned with the radial slots of the inner barrel, and a biased closed position in which the radial slots of the outer barrel and inner barrel are out of radial alignment and configured to constrict the body lumen at two locations along the length thereof; and
    wherein the fastener includes a biasing element, and the outer barrel and the inner barrel are biased to one of the closed position and the open position without the biasing element obstructing any of the radial slots.

2. The surgical fastener according to claim 1, wherein each of the outer and inner barrels has an end wall provided at a proximal end thereof and has an open distal end.

3. The surgical fastener according to claim 2, wherein the slots in each of the outer and inner barrels extend through their respective open distal ends.

4. The surgical fastener according to claim 3, wherein the end wall of the inner barrel includes a central opening formed therethrough and a nub extending from a proximal surface of the end wall, the nub being configured and dimensioned to be received within the central opening formed in the end wall of the outer barrel.

5. The surgical fastener according to claim 4, further including a biasing element disposed about the nub of the inner barrel for biasing the inner and outer barrels to the closed position, the biasing element including a first leg in operative engagement with the slot defined by the protrusion of the outer barrel and a second leg in operative engagement with the nub of the inner barrel.

6. The surgical fastener according to claim 5, further including a release rod configured and dimensioned to be removably received within a release hole formed in each of the end walls of the inner and outer barrels, wherein when the release rod is received within the release holes, the fastener is maintained in the biased open position.

7. The surgical fastener according to claim 5, wherein the central opening of the end wall of the outer barrel includes at least one stop extending radially inward from an inner edge of the central opening and wherein the nub of the inner barrel includes at least one lug extending radially outward therefrom, wherein the lug engages the stop in order to prevent free rotation of the inner and outer barrels with respect to one another.

8. The surgical fastener according to claim 6, wherein the shape of the slots is selected from the group consisting of rectangular, tapered, helical and tear-drop.

9. The surgical fastener according to claim 8, wherein the slots have longitudinal edges, and the longitudinal edges of the slots of the inner and outer barrels in the biased closed position terminate fluid flow through the constricted lumen atraumatically.

10. The surgical fastener according to claim 2, wherein the end wall of the outer barrel includes a central opening formed therethrough and the end wall of the inner barrel includes a snap-fit type engagement member extending outwardly therefrom and through the central opening, such that the engagement member of the inner barrel is snap-fit into and engaged with the central opening of the end wall of the outer barrel.

11. The surgical fastener according to claim 10, further including a rotatable biasing element disposed about the snap-fit type engagement member for rotatably biasing the inner and outer barrels to the closed position, the biasing element including a first leg for engaging a stop member formed on an outer surface of the end wall of the inner barrel and a second leg for engaging a stop member formed on an inner surface of the end wall of the outer barrel.

12. The surgical fastener according to claim 10, further including a release rod configured and dimensioned to be removably received within a release hole formed in each of the end walls of the inner and outer barrels, the release holes being radially aligned with one another and the release rod being received within the release holes to maintain the inner and outer barrels of the fastener biased in the open position.

13. The surgical fastener according to claim 12, wherein each outer and inner barrel has an end wall provided at a proximal end thereof and has an open distal end in communication with the radial slot of the respective barrels, and wherein the alignment mechanism includes a hole formed in each end wall, the holes being axially alignable when the barrels are in the open position.

14. The surgical fastener according to claim 10, wherein the outer barrel includes an annular rim extending proximally from the end wall, and the annular rim includes a protrusion extending radially inward therefrom and defining a stop therein.

15. The surgical fastener according to claim 14, wherein the stop includes an undercut therein.

16. The surgical fastener according to claim 1, wherein there is included an alignment mechanism operatively coupled to the inner and outer barrels to maintain the barrels in alignment and biased in the open position.

17. The surgical fastener according to claim 16, wherein the alignment mechanism includes a rod configured and dimensioned to pass through the respective holes when the barrels are in the biased open position, to releasably maintain the barrels in the biased open position.

18. The surgical fastener according to claim 1, wherein the shape of the slots is selected from the group consisting of rectangular, tapered, helical and tear-drop.

19. The surgical fastener according to claim 18, wherein the slots have longitudinal edges, and the longitudinal edges of the slots of the inner and outer barrels when in the biased closed position terminate fluid flow through the constricted lumen atraumatically.

20. The surgical fastener according to claim 1, wherein the inner barrel is concentric relative to the outer barrel.

21. A surgical fastener for terminating a flow of fluid through a body lumen, comprising:
an outer barrel having an annular side wall including at least a pair of open ended radial slots formed therein;
an inner barrel rotatably coupled within the outer barrel, the inner barrel having an annular side wall including a pair of open ended radial slots formed therein, each radial slot of the pair formed in the side wall of the inner barrel corresponding to a respective one of the radial slots formed in the outer barrel; and a biasing element for rotatably biasing the inner barrel and the outer barrel relative to one another without the biasing element obstructing any of the radial slots;
wherein the assembled surgical fastener has a biased open position in which the radial slots of the outer barrel are radially aligned with the radial slots of the inner barrel to define open ended slots, a biased closed position in which the radial slots of the outer barrel and inner barrel are out of radial alignment and configured to constrict the body lumen at two locations along the length thereof between side edges of the radial slots of the inner and outer barrels.

22. A surgical fastener for terminating a flow of fluid through a body lumen, comprising:
an outer barrel having an annular side wall including at least a pair of radial slots formed therein and defining an open end; and
an inner barrel rotatably coupled within the outer barrel, the inner barrel having an annular side wall including a pair of radial slots formed therein and defining an open end, wherein the coupled inner and outer barrels are open ended in a common direction, each radial slot of the pair formed in the side wall of the inner barrel corresponding to a respective one of the radial slots formed in the outer barrel;
wherein the surgical fastener has a biased open position in which the radial slots of the outer barrel are radially aligned with the radial slots of the inner barrel, and a biased closed position in which the radial slots of the outer barrel and inner barrel are out of radial alignment and configured to constrict the body lumen at two locations along the length thereof;
wherein each of the outer and inner barrels has an end wall provided at a proximal end thereof and has an open distal end; and
wherein the end wall of the outer barrel includes a central opening formed therethrough and the end wall of the inner barrel includes a snap-fit type engagement member extending outwardly therefrom and through the central opening, such that the engagement member of the inner barrel is snap-fit into and engaged with the central opening of the end wall of the outer barrel.

23. The surgical fastener according to claim 22, further including a rotatable biasing element disposed about the snap-fit type engagement member for rotatably biasing the inner and outer barrels to the closed position, the biasing element including a first leg for engaging a stop member formed on an outer surface of the end wall of the inner barrel and a second leg for engaging a stop member formed on an inner surface of the end wall of the outer barrel.

24. The surgical fastener according to claim 22, further including a release rod configured and dimensioned to be removably received within a release hole formed in each of the end walls of the inner and outer barrels, the release holes being radially aligned with one another and the release rod being received within the release holes to maintain the inner and outer barrels of the fastener biased in the open position.

25. The surgical fastener according to claim 24, wherein each outer and inner barrel has an end wall provided at a proximal end thereof and has an open distal end in communication with the radial slot of the respective barrels, and wherein the alignment mechanism includes a hole formed in each end wall, the holes being axially alignable when the barrels are in the open position.

26. The surgical fastener according to claim 22, wherein the outer barrel includes an annular rim extending proximally from the end wall, and the annular rim includes a protrusion extending radially inward therefrom and defining a stop therein.

27. The surgical fastener according to claim 26, wherein the stop includes an undercut therein.

28. A surgical fastener for terminating a flow of fluid through a body lumen, comprising:
- an outer barrel having an annular side wall including at least a pair of radial slots formed therein and defining an open end; and
- an inner barrel rotatably coupled within the outer barrel, the inner barrel having an annular side wall including a pair of radial slots formed therein and defining an open end, wherein the coupled inner and outer barrels are open ended in a common direction, each radial slot of the pair formed in the side wall of the inner barrel corresponding to a respective one of the radial slots formed in the outer barrel;
- wherein the surgical fastener has a biased open position in which the radial slots of the outer barrel are radially aligned with the radial slots of the inner barrel, and a biased closed position in which the radial slots of the outer barrel and inner barrel are out of radial alignment and configured to constrict the body lumen at two locations along the length thereof;
- wherein each of the outer and inner barrels has an end wall provided at a proximal end thereof and has an open distal end;
- wherein the slots in each of the outer and inner barrels extend through their respective open distal ends; and
- wherein the end wall of the inner barrel includes a central opening formed therethrough and a nub extending from a proximal surface of the end wall, the nub being configured and dimensioned to be received within the central opening formed in the end wall of the outer barrel.

29. The surgical fastener according to claim 28, further including a biasing element disposed about the nub of the inner barrel for biasing the inner and outer barrels to the closed position, the biasing element including a first leg in operative engagement with the slot defined by the protrusion of the outer barrel and a second leg in operative engagement with the nub of the inner barrel.

30. The surgical fastener according to claim 29, further including a release rod configured and dimensioned to be removably received within a release hole formed in each of the end walls of the inner and outer barrels, wherein when the release rod is received within the release holes, the fastener is maintained in the biased open position.

31. The surgical fastener according to claim 29, wherein the central opening of the end wall of the outer barrel includes at least one stop extending radially inward from an inner edge of the central opening and wherein the nub of the inner barrel includes at least one lug extending radially outward therefrom, wherein the lug engages the stop in order to prevent free rotation of the inner and outer barrels with respect to one another.

32. The surgical fastener according to claim 30, wherein the shape of the slots is selected from the group consisting of rectangular, tapered, helical and tear-drop.

33. The surgical fastener according to claim 32, wherein the slots have longitudinal edges, and the longitudinal edges of the slots of the inner and outer barrels in the biased closed position terminate fluid flow through the constricted lumen atraumatically.

34. A surgical fastener for terminating a flow of fluid through a body lumen, comprising:
- an outer barrel having an annular side wall including at least a pair of radial slots formed therein and defining an open end; and
- an inner barrel rotatably coupled within the outer barrel, the inner barrel having an annular side wall including a pair of radial slots formed therein and defining an open end, wherein the coupled inner and outer barrels are open ended in a common direction, each radial slot of the pair formed in the side wall of the inner barrel corresponding to a respective one of the radial slots formed in the outer barrel;
- wherein the surgical fastener has a biased open position in which the radial slots of the outer barrel are radially aligned with the radial slots of the inner barrel, and a biased closed position in which the radial slots of the outer barrel and inner barrel are out of radial alignment and configured to constrict the body lumen at two locations along the length thereof;
- wherein there is included an alignment mechanism operatively coupled to holes in the inner and outer barrels to maintain the barrels in alignment and biased in the open position; and
- wherein the alignment mechanism includes a rod configured and dimensioned to pass through the holes when the barrels are in the biased open position, to releasably maintain the barrels in the biased open position.

* * * * *